US011701455B2

(12) United States Patent
Grunlan et al.

(10) Patent No.: US 11,701,455 B2
(45) Date of Patent: Jul. 18, 2023

(54) SELF-CLEANING MEMBRANE FOR MEDICAL DEVICES

(71) Applicant: The Texas A&M University System, College Station, TX (US)

(72) Inventors: Melissa A. Grunlan, College Station, TX (US); Gerard L. Cote, College Station, TX (US); Alexander A. Abraham, College Station, TX (US); Ruochong Fei, College Station, TX (US); Andrea K. Locke, College Station, TX (US)

(73) Assignee: The Texas A&M University System, College Station, TX (US)

( * ) Notice: Subject to any disclaimer, the term of this patent is extended or adjusted under 35 U.S.C. 154(b) by 273 days.

(21) Appl. No.: 15/545,811

(22) PCT Filed: Jan. 27, 2016

(86) PCT No.: PCT/US2016/015088
§ 371 (c)(1),
(2) Date: Jul. 24, 2017

(87) PCT Pub. No.: WO2016/123197
PCT Pub. Date: Aug. 4, 2016

(65) Prior Publication Data
US 2018/0021483 A1    Jan. 25, 2018

Related U.S. Application Data

(60) Provisional application No. 62/108,377, filed on Jan. 27, 2015.

(51) Int. Cl.
*A61B 5/1473*    (2006.01)
*A61B 5/145*    (2006.01)
(Continued)

(52) U.S. Cl.
CPC .......... *A61L 31/048* (2013.01); *A61B 5/1473* (2013.01); *A61B 5/14532* (2013.01);
(Continued)

(58) Field of Classification Search
CPC ...... A61L 31/048; A61L 31/10; A61L 31/145; A61B 5/14532; A61B 5/1473; C08F 220/56; C08L 33/26; C08L 2203/02
See application file for complete search history.

(56) References Cited

U.S. PATENT DOCUMENTS 6,497,729 B1 * 12/2002 Moussy .............. A61B 5/0031
623/23.57
2004/0007051 A1    1/2004 Bashir et al.
(Continued)

FOREIGN PATENT DOCUMENTS

WO    2006102762    10/2006

OTHER PUBLICATIONS

Gant, R. M., et al. "Design of a self-cleaning thermoresponsive nanocomposite hydrogel membrane for implantable biosensors." Acta biomaterialia 6.8 (2010): 2903-2910 (Year: 2010).*
(Continued)

*Primary Examiner* — Andrey Shostak
(74) *Attorney, Agent, or Firm* — Tumey L.L.P.

(57) ABSTRACT

The disclosure provides a method for cleaning an implanted medical device. In one embodiment, the method includes providing a medical device including a membrane; wherein the membrane comprises a thermoresponsive hydrogel including N-isopropylacrylamide (NIPAAm) or poly(N-isopropylacrylamide) (PNIPAAm), and a volume phase transition temperature (VPTT). The method also includes implanting the medical device into a target area; wherein the membrane temperature is maintained at substantially the same temperature as the target area; wherein temperature
(Continued)

fluctuations within the target area that approach, meet and/or exceed the volume phase transition temperature induce deswelling or relative deswelling in the membrane and temperature fluctuations within the target area that are relatively lower and/or approach and/or fall below the volume phase transition temperature induce swelling or relative swelling in the membrane.

7 Claims, 6 Drawing Sheets

(51) Int. Cl.
    *A61L 31/04*     (2006.01)
    *A61L 31/10*     (2006.01)
    *C08L 33/26*     (2006.01)
    *C08F 220/56*     (2006.01)
    *A61L 31/14*     (2006.01)

(52) U.S. Cl.
    CPC ............. *A61L 31/10* (2013.01); *A61L 31/145* (2013.01); *C08F 220/56* (2013.01); *C08L 33/26* (2013.01); *C08L 2203/02* (2013.01)

(56) References Cited

U.S. PATENT DOCUMENTS

| | | | |
|---|---|---|---|
| 2006/0135911 A1 | 6/2006 | Mittur | |
| 2006/0235176 A1* | 10/2006 | Lee | C08F 220/56 526/264 |
| 2010/0056894 A1* | 3/2010 | Cote | A61B 5/14532 600/365 |
| 2011/0256628 A1* | 10/2011 | Galperin | A61L 27/3804 435/396 |
| 2015/0376594 A1* | 12/2015 | Walker | C12Q 1/54 435/14 |

OTHER PUBLICATIONS

George et al., "Thermoresponsive double network hydrogels with improved mechanical properties", Dept. of Biomedical Engineering, Texas A&M University, dated Mar. 25, 2012, presented to 243 ACS National Meeting, San Diego, Mar. 25-29, 2012, pp. 1-16 (Year: 2012).*
"Building an implantable glucose biosensor," presented at SFB Biomaterials Day at Rice University Meeting by Means et al. Dated 2012. (Year: 2012).*
Fei, Ruochong, et al. "Ultra-strong thermoresponsive double network hydrogels." Soft Matter 9.10 (2013): 2912-2919 (Year: 2013).*
"Thermoresponsive double network micropillared hydrogels for cell release" in Macromolecular Biosciences by Fei et al. Dated May 2014.
"A self-cleaning membrane to extend the lifetime of an implanted glucose biosensor" in ACS Appl. Mater. & Interfaces by Abraham et al. Dated 2013.
"Ultra strong thermoresponsive hydrogels" in Soft Matter by Fei et al. Dated 2013.
"Thermoresponsive nanocomposite double network nanocomposite hydrogels" in Soft Matter by Fei et al. Dated 2012.
"Thermoresponsive nanocomposite hydrogels: Transparency, rapid deswelling and cell release" in J. Biomat. Tissue Eng. by Gant et al. Dated 2011.
"Design of a self-cleaning thermoresponsive nanocomposite hydrogel membrane for implantable biosensors" in Acta Biomaterialia by Gant et al. Dated 2010.
"Micropatterning of poly(N-isopropylacrylamide) PNIPAAm hydrogels: Effects of thermosensitivity and cell release behavior" in Sensors and Material by Hou et al. Dated 2010.
"A thermoresponsive hydrogel poly(N-isopropylacrylamide) micropatterning method using microfluidics techniques" in J. Micromech. Microeng. by Hou et al. Dated 2009.
"Development of a self-cleaning sensor membrane for implantable biosensors" in J. Biomed. Mater. Res. by Gant et al. Dated 2009.
"Thermoresponsive nanocomposite hydrogels with cell-releasing behavior" in Biomaterials by Hou et al. Dated 2008.
"Ultra strong, thermoresponsive double-network hydrogels" in PMSE Preprints by Fei et al. Dated 2012.
"Thermoresponsive double network hydrogels with improved mechanical properties" in POLY Preprints by George et al. Dated 2012.
"Thermoresponsive nanocomposite double network hydrogels" in POLY Preprints by Fei et al. Dated 2010.
"Thermoresponsive nanocomposite hydrogels with cell-releasing behavior" in POLY Preprints by Hou et al. Dated 2009.
"Self-cleaning membrane for increased lifetime of subcutaneous glucose biosensors" presented at 247th ACS National Meeting by Fei et al. Dated 2014.
"Ultra strong, thermoresponsive double-network hydrogels" presented at TAMU Eng-Life Workshop by Fei et al. Dated 2013.
"Nanocomposite self-cleaning membranes for implanted glucose biosensors" presented at Composites at Lake Louise meeting by Grunlan. Dated 2013.
"Self-cleaning membranes for implanted glucose biosensors" presented at BMES National Meeting by Means et al. Dated 2013.
"Self-cleaning membranes for implanted glucose biosensors" presented at MRS-Singapore ICMAT Conference by Grunlan et al. Dated 2013.
"Self-cleaning membranes for implanted glucose biosensors" presented at European Polymer Conference by Grunlan et al. Dated 2013.
"High strength thermoresponsive double network" presented at 245th ACS National Meeting by Grunlan et al. Dated 2013.
"Subcutaneous glucose biosensor I: a self-cleaning membrane for increased lifetime" presented at Workshop on Innovation Towards an Artificial Pancreas by Fei et al. Dated 2013.
"Ultra strong, thermoresponsive double-network hydrogels" presented at SFB Annual Meeting & Exposition by Fei et al. Dated 2013.
"Self-cleaning membranes for implanted glucose biosensors" presented at Dept. of Chemistry and Biochemistry by Grunlan et al. Dated 2013.
"A thermoresponsive nanocomposite double network hydrogel membrane to control biofouling" presented at National BMES Meeting by Abraham et al. Dated 2012.
"Ultra strong, thermoresponsive double-network hydrogels" presented at SFB Biomaterials Day at Rice University Meeting by Fei et al. Dated 2012.
"Building an implantable glucose biosensor" presented at SFB Biomaterials Day at Rice University Meeting by Means et al. Dated 2012.
"Nanocomposite Hydrogels" presented at 2012 IPRIME by Grunlan. Dated 2012.
"Self-cleaning membranes for implanted glucose biosensors" presented to Dept. of Chemistry by Grunlan. Dated 2012.
"Thermoresponsive double network hydrogels: Introduction of electrostatic forces" presented at SFB Biomaterials Day at Texas A&M University Meeting by Park et al. Dated 2011.
"Thermoresponsive double network hydrogels with improved mechanical properties" presented at 243rd ACS National Meeting by George et al. Dated 2012.
"Thermoresponsive double network hydrogels: Introduction of electrostatic forces" presented at SFB Biomaterials Day at Texas A&M University Meeting by Fei et al. Dated 2011.
"Dimensional changes of thermoresponsive biosensor membrane via optical tomography and microscopy" presented at BMES National Meeting by Abraham et al. Dated 2011.
"Self-cleaning sensor membranes based on thermoresponsive nanocomposite hydrogels" presented at Fall 2010 MRS National Meeting by Grunlan et al. Dated 2010.

(56) References Cited

OTHER PUBLICATIONS

"Thermoresponsive nanocomposite hydrogels as self-cleaning membranes for glucose biosensors" presented at Polymer Chemistry Conference by Grunlan et al. Dated 2010.

"Self-cleaning micropatterned nanocomposite hydrogels" presented at BMES National Meeting by George et al. Dated 2010.

"Thermoresponsive nanocomposite double network hydrogels with cell-releasing behavior" presented at BMES National Meeting by Fei et al. Dated 2010.

"Thermoresponsive nanocomposite hydrogels as self-cleaning membranes for glucose biosensors" presented at BMES National Meeting by Grunlan et al. Dated 2010.

"Optimizing the design of a self-cleaning thermoresponsive hydrogel membrane for glucose sensing" presented at BMES National Meeting by Abraham et al. Dated 2010.

"Thermoresponsive nanocomposite double network hydrogels" presented at 240th ACS Meeting by Fei et al. Dated 2010.

"Optimization of an implantable self-cleaning thermoresponsive nanocomposite hydrogel sensor membrane" presented at BMES National Meeting by Abraham et al. Dated 2009.

"Development of a self-cleaning membrane for implantable glucose biosensors" presented at Fall 2008 MRS National Meeting by Gant et al. Dated 2008.

"Introduction of polysiloxane nanoparticles and polysiloxane star polymers into thermoresponsive poly(N-isopropylacrylamide) (PNIPAAm) hydrogels" presented at Fall 2008 MRS National Meeting by Hou et al. Dated 2008.

"Thermoresponsive composite hydrogels with cell-releasing properties" presented at Spring 2008 MRS Meeting by Grunlan et al. Dated 2008.

"Thermoresponsive composite hydrogels: Micropatterning and self-cleaning behavior" presented at Spring 2007 MRS Meeting by Grunlan et al. Dated 2008.

International Search Report and Written Opinion for PCT/US2016/015088 dated May 16, 2016.

International Preliminary Report for PCT/US2016/015088 dated Aug. 1, 2017.

"Self-cleaning membranes based on thermoresponsive double network hydrogels" a dissertation by Fei. Dated 2014.

Extended European Search Report for Application No. 16744019.7 dated Sep. 7, 2018.

* cited by examiner

SELF-CLEANING MEMBRANE FOR MEDICAL DEVICES

CROSS-REFERENCE TO RELATED APPLICATIONS

This application claims the benefit of U.S. Provisional Application No. 62/108,377, filed Jan. 27, 2015, which is incorporated by reference in its entirety.

STATEMENT REGARDING FEDERALLY SPONSORED RESEARCH OR DEVELOPMENT

This invention was made with government support under 1R01DK095101-01A1 and 1R21DK082930-01A1 awarded by the National Institutes of Health. The government has certain rights in the disclosure.

BACKGROUND OF THE DISCLOSURE

Field of the Disclosure

The present embodiments relate to self-cleaning membranes, and more particularly, to using self-cleaning membranes for implantable medical devices.

Background of the Disclosure

Implantable medical devices may be used for a wide variety of applications, including, for example, implantable sensors for continuous glucose monitoring. Implantable sensors may be desirable because, after an initial implantation, they may have the potential for continuous detection of the analyte of interest, for example, glucose. Existing implantable sensors and other medical devices may use daily calibration and/or generally may have limited lifespans. The loss of sensor or medical device sensitivity, efficacy and lifetime may be attributed to the foreign body reaction and associated biofouling. In the case of implantable sensors, biofouling may diminish analyte diffusion and/or signal propagation. In addition, a transdermal sensor with a tethered design may be used to aide in frequent removal and replacement of the biofouled device. Thus, transdermal and/or subcutaneously implanted sensors or other implanted medical devices that overcome the noted deficiencies may be desired. To improve functionality for such an implantable sensor or medical device, it may be important to limit biofouling.

Non-toxic, cytocompatible materials may still elicit a host response. However, the degree and longevity of that response may be dependent on a variety of factors, including, for example, material structure and morphology, implant size, implantation site, material biodegradability, and the host's sensitivity to the material. Upon implantation, an inflammatory response may be triggered that results in a surge of specialized immune cells primarily consisting of neutrophils and macrophages. Depending on one or more of the factors previously listed, the acute inflammatory response may become chronic. This condition may exhibit an increase in fibroblast cell population that may begin to form an organized, collagenous tissue capsule adjacent to the surface of the implantable medical device within about one to two weeks. The extent of the foreign body reaction and related biofouling may decrease diffusion of the target analyte as well as diminish signal strength, and thereby reducing sensor accuracy.

Consequently, there may be a need for transdermal and/or subcutaneously implanted medical devices with increased sensitivity, efficacy and lifetime that are capable of mitigating the effects of biofouling.

BRIEF SUMMARY OF SOME OF THE PREFERRED EMBODIMENTS

These and other needs in the art are addressed in a further embodiment by a method for cleaning a transdermal or subcutaneously implanted glucose biosensor providing a glucose biosensor comprising a double network membrane comprising a first network and a second network; wherein the glucose biosensor measures the concentration of glucose; wherein the membrane comprises a thermoresponsive hydrogel comprising N-isopropylacrylamide, one or more polysiloxane colloidal nanoparticles, a comonomer of N-vinylpyrrolidone, and a volume phase transition temperature. The method further comprises implanting the medical device into a target area; wherein the membrane temperature is maintained at substantially the same temperature as the target area; wherein temperature fluctuations within the target area that exceed the volume phase transition temperature induce deswelling in the membrane and temperature fluctuations within the target area that fall behind the volume phase transition temperature induce swelling in the membrane.

These and other needs in the art are addressed in a further embodiment by a method for cleaning a transdermal or subcutaneously implanted glucose biosensor providing a glucose biosensor comprising a double network membrane comprising a first network and a second network; wherein the glucose biosensor measures the concentration of glucose; wherein the membrane comprises a thermoresponsive hydrogel comprising N-isopropylacrylamide, one or more polysiloxane colloidal nanoparticles, a comonomer of N-vinylpyrrolidone, and a volume phase transition temperature. The method further comprises implanting the medical device into a target area; wherein the membrane temperature is maintained at substantially the same temperature as the target area; wherein temperature fluctuations within the target area that exceed the volume phase transition temperature induce deswelling in the membrane and temperature fluctuations within the target area that fall behind the volume phase transition temperature induce swelling in the membrane.

The foregoing has outlined rather broadly the features and technical advantages of the present disclosure in order that the detailed description of the disclosure that follows may be better understood. Additional features and advantages of the disclosure will be described hereinafter that form the subject of the claims of the disclosure. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

For a detailed description of the preferred embodiments of the disclosure, reference will now be made to the accompanying drawings in which.

DETAILED DESCRIPTION OF THE PREFERRED EMBODIMENTS

The present embodiments relate to self-cleaning membranes, and more particularly, to self-cleaning membranes for implantable medical devices. In embodiments, the self-cleaning membranes comprise thermoresponsive hydrogels. The thermoresponsive hydrogels may provide a self-cleaning sensor membrane for an implantable medical device (e.g., a transdermal or subcutaneously implanted biosensor or continuous glucose monitor). At temperatures that approach, meet and/or are above the volume phase transition temperature (VPTT) (i.e. approach, meet and/or are above resting/normal body temperature for a particular location in the body) (e.g. ~38° C.), the thermoresponsive hydrogel may deswell and/or become relatively more deswollen and, as a result, become relatively more hydrophobic. Thus, at resting/normal body temperatures for a particular location in the body (e.g., ~35° C. for subcutaneous tissue of the wrist), the thermoresponsive hydrogel may be swollen or relatively more swollen and, as a result, relatively more hydrophilic. Therefore, the thermoresponsive hydrogel membrane may be capable of cyclical deswelling and reswelling which may induce self-cleaning (i.e. removal of some or all biofouling products) as body temperatures fluctuate between those approaching, meeting and/or exceeding the VPTT and those that are relatively lower and/or approach and/or fall below the VPTT. Cycling the temperature of the thermoresponsive hydrogels around the VPTT has been shown to cause detachment of cells. In accordance with observed results, removal of biofouling products (e.g., fibroblast cells) may lead to a substantial increase in diffusion of the analyte.

Figure 1A:
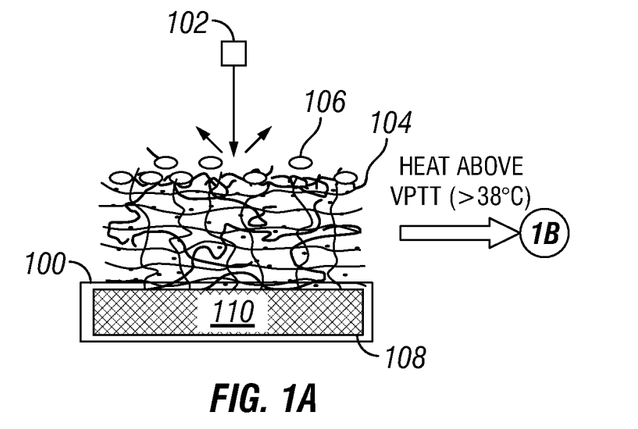
FIGS. 1A)-C) illustrates thermocycling stages for a self-cleaning sensor membrane in accordance with embodiments.
Figure 1B:
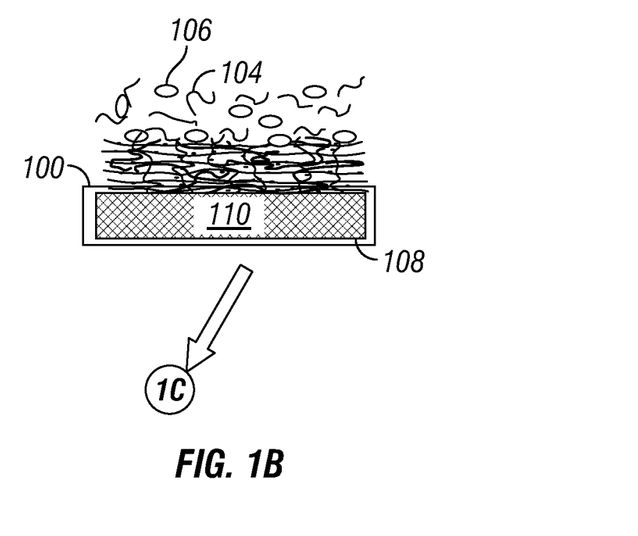
Figure 1C:
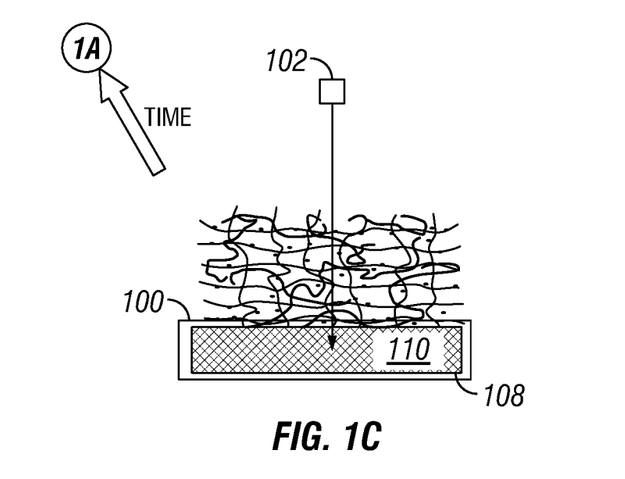

FIG. 1 illustrates an embodiment of events that may occur during a thermal cycle of an enclosed glucose sensor 108 including a glucose sensing assay material 110 and a thermoresponsive hydrogel membrane 100, which may be used for an implantable medical device (e.g., a transdermal or subcutaneously implanted biosensor or continuous glucose monitor). As the thermoresponsive hydrogel membrane 100 accumulates proteins 104 and cells 106 from the physiological environment, the diffusion of analytes 102 (e.g., glucose as shown in FIG. 1A-C) may be reduced. Conventional sensor membranes may require the replacement of the sensor at this stage. The thermoresponsive hydrogel membrane 100 may begin to deswell as its temperature approaches the VPTT (e.g., above 38° C.). It may continue to deswell as its temperature exceeds the VPTT. This physical collapse and change in surface properties may disrupt adhesion of proteins 104 and cells 106 as shown in FIG. 1B. Upon cooling back to ~35° C. (i.e. about normal/resting body temperature of the subcutaneous tissue of the wrist), the thermoresponsive hydrogel sensor membrane 100 may return to a relatively more swollen state, as shown in FIG. 1C. In some embodiments, the reversion to the relatively more swollen state may add further disruption to the adhesion of proteins 104 or cells 106. Analyte diffusion may be restored through the clean, "expanded" (i.e. relatively more swollen) thermoresponsive hydrogel membrane 100 to the enclosed glucose sensor 108 or glucose sensing assay material 110 as shown in FIG. 1C. Its mechanical properties may allow the enclosed glucose sensor 108 to be placed in vivo without breakage (and eventually removed without breakage as well).

Figure 2A:
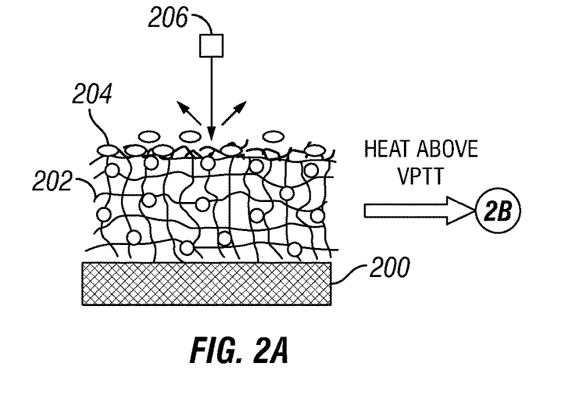
FIG. 2A)-C) illustrates another example of the thermocycling stages for a self-cleaning sensor membrane in accordance with embodiments.
Figure 2B:
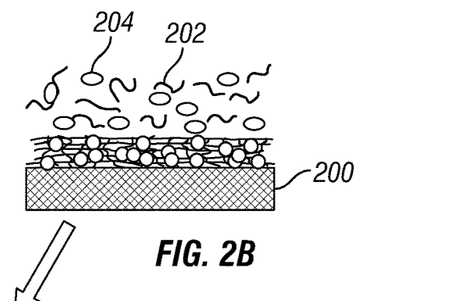
Figure 2C:
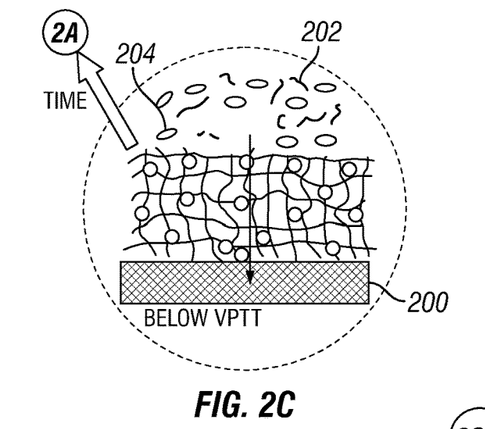
Figure 2C:
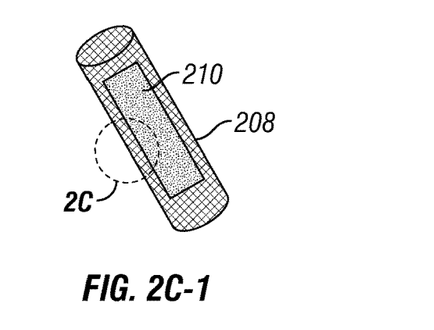
Figure 2C:
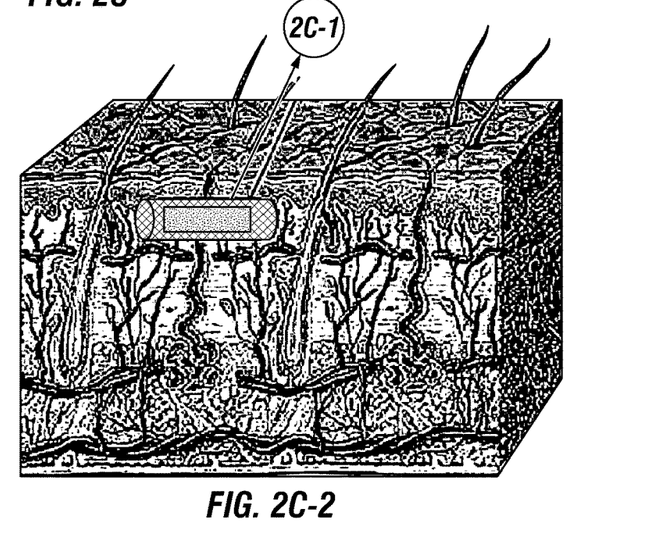

FIGS. 2A-C illustrate events that may occur during a thermal cycle of an enclosed glucose sensor 208 including a glucose sensing assay material 210 and a thermoresponsive hydrogel membrane 200, which may be used for an implantable medical device (e.g., a transdermal or subcutaneously implanted biosensor or continuous glucose monitor). The embodiment illustrated in FIGS. 2A-C comprises a thermoresponsive hydrogel membrane 200 comprising nanoparticles. Over time, the thermoresponsive hydrogel membrane 200 may accumulate proteins 202 and cells 204 from the physiological environment thereby reducing diffusion of analytes 206 (e.g., glucose) as shown in FIG. 2A. Conventional sensor membranes may require the replacement of the sensor at this stage. The thermoresponsive hydrogel membrane 200 may begin to deswell as its temperature approaches the VPTT (e.g., above 38° C.). It may continue to deswell as its temperature exceeds the VPTT. This physical collapse and change in surface properties may disrupt adhesion of proteins 202 and cells 204 as shown in FIG. 2B. Upon cooling back to ~35° C. (i.e. about normal/resting body temperature of the subcutaneous tissue of the wrist), a thermoresponsive hydrogel sensor membrane 200 may return to a relatively more swollen state, as shown in FIG. 2C. The reversion to the relatively more swollen state may add further disruption to the adhesion of proteins 202 and cells 204. This physical swelling or reswelling and change of surface properties may disrupt the adhesion of proteins 202, shown in FIG. 2B. Analyte diffusion may be restored through the clean, "expanded" (i.e. relatively more swollen) membrane to the enclosed glucose sensor 208 or glucose sensing assay material 210 as shown in FIG. 2C. Its mechanical properties may allow the enclosed glucose sensor 208 to be placed in vivo without breakage (and eventually removed without breakage as well).

The thermoresponsive hydrogels may comprise poly(N-isopropylacrylamide) ("PNIPAAm") or N-isopropylacrylamide ("NIPAAm"). Additionally, one or more monomers may be used in conjunction with (e.g. copolymerized with) PNIPAAM and/or NIPAAm. An example of one such monomer is 2-acrylamido-2-methylpropane sulfonic acid (AMPS). For example, in an embodiment, a double network (DN) thermoresponsive hydrogel comprising a relatively tightly cross-linked, ionized 1$^{st}$ network [P(NIPAAm-co-AMPS)] and a relatively loosely cross-linked, interpenetrating 2$^{nd}$ network [PNIPAAm] may be used as self-cleaning membrane. Incorporation of the additional monomer may be done in any ratio in order to achieve the desired effect on thermosensitivity and mechanical properties (e.g. compressive strength). For example, varying levels of AMPS may be incorporated in the 1$^{st}$ or 2$^{nd}$ network, as an example, the ratio of AMPS:NIPAAm may be about 0:100 to about 75:25 wt %.

Embodiments of the thermoresponsive hydrogel may comprise a single network (SN) or a DN hydrogel composed of an interpenetrating, asymmetrically cross-linked PNIPAAm matrix with nanoparticles incorporated during the formation of the first network or second network in embodiments comprising a DN. An example of a nanoparticle includes, but should not be limited to, polysiloxane and the like. The nanoparticles may range in size from about 10 nm to about 300 nm, alternatively about 50 nm to about 200 nm, or further alternatively about 100 nm to about 150 nm based on the desired application. The nanoparticles may comprise a mixture of sizes as desired.

In embodiments, the thermoresponsive hydrogel, whether an SN or a DN is tailored to respond to body temperature fluctuations that may be induced physiologically and/or environmentally. This may, in some embodiments, eliminate the need for an externally controlled temperature regulation device or method outside of the target or host. Additionally, size and/or geometry of the thermoresponsive hydrogel may be used to further tailor the design to meet the desired thermosensitivity. For example, a cylindrical thermoresponsive hydrogel comprising a diameter of about 1.5 mm and a length of 5 mm may be used in embodiments.

In embodiments, one or more comonomers may be desirable to set and/or adjust the VPTT to a precise value or range of values (e.g., ~38° C.). For instance, the VPTT of PNIPAAm-based hydrogels may be adjusted by the incorporation of hydrophobic comonomers or hydrophilic comonomers. An example of a hydrophilic co-monomer is N-vinylpyrrolidone ("NVP"). Hydrogels may be formed from curing aqueous (or non-aqueous) precursor solutions comprised of (1)N-isopropylacrylamide ("NIPAAm") monomer and optionally comonomer(s) or (2) PNIPAAm polymer and optionally copolymers of PNIPAAm (e.g. copoly(N-isopropylacrylamide-acrylic acid) ("NIPAAm-co-AA")) or some combination thereof. A crosslinker(s) such as N,N'-methylenebisacrylamide may or may not be included to provide crosslinking. The comonomer may be included in any sufficient amount to adjust the VPTT of the thermoresponsive hydrogel to the desired value. For example, a 1-2 wt % of the NVP comonomer, based on NIPAAm wt %, may be used to adjust the VPTT value of a PNIPAAm DN hydrogel membrane comprising an interpenetrating, asymmetrically crosslinked PNIPAAm matrix with polysiloxane nanoparticles (~200 nm diameter) embedded during the formation of the 1$^{st}$ network to a VPTT value of ~38° C. As such, in addition to the methods discussed above, inclusion of a comonomer may also be used to adjust the VPTT value or range of values to suit a desired application.

Figure 3A:
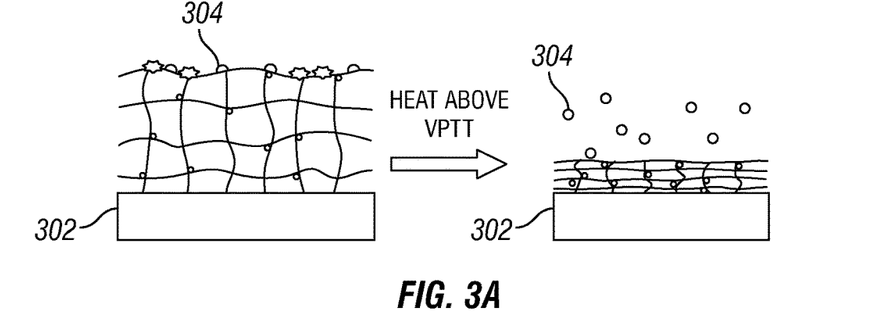
FIG. 3A illustrates a hydrogel in a swollen, hydrophilic state below the VPTT with attached acclimated cells in accordance with embodiments.

FIG. 3A illustrates a thermoresponsive hydrogel membrane 302 in a relatively swollen, hydrophilic state below the VPTT (or at relatively lower temperatures so as to induce some degree of swelling) with attached acclimated cells 304 in accordance with embodiments.

Figure 3B:
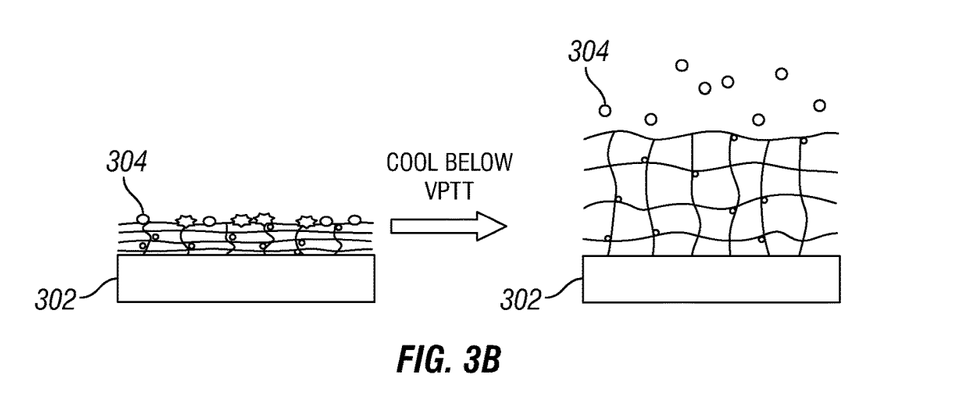
FIG. 3B illustrates a hydrogel in a dehydrated, hydrophobic state above the VPTT with acclimated cells in accordance with embodiments.

FIG. 3B illustrates a thermoresponsive hydrogel membrane 302 in a relatively dehydrated, hydrophobic state approaching, meeting and or exceeding the VPTT with acclimated cells 304 in accordance with embodiments. As discussed above, an implantable medical device (e.g., a biosensor) may be configured and arranged with a thermoresponsive hydrogel membrane 302 to reduce and/or minimize the biofouling associated with the foreign body reaction. The thermoresponsive hydrogel membrane 302 may have, in some embodiments, a volume phase transition temperature just above body temperature (e.g., at about 38° C.). The thermoresponsive hydrogel membrane 302 may comprise about 1 to about 2 wt % NVP by weight of any other monomers (e.g. NIPAAm). A thermoresponsive hydrogel membrane 302, according to some embodiments, may release up to about 10-40%, up to about 40-70%, up to about 70-80% of the initially attached fibroblast cells when the temperature is decreases below the VPTT. In some embodiments, the thermoresponsive hydrogel membrane 302 may experience little or no significant reattachment during subsequent thermocycles. The thermoresponsive hydrogel membrane 302, according to some embodiments, may reduce and/or prevent capsule formation. Embodiments comprise implantable medical devices. For example, the thermoresponsive hydrogel membrane 302 disclosed herein, may be used as self-cleaning membrane for biosensor, glucose monitors, water filtration membranes, hemodialysis catheters, and the like. Further, embodiments, contemplate wearable biosensors, and thus, it is to be understood that embodiments of the self-cleaning membranes are not to be limited to transdermal and subcutaneous applications. The thermoresponsive hydrogel membrane described herein may be "self-cleaning" and may employ an active or "cell-releasing" method to physically detach adsorbed cells from its surface without an external heating source. The "cell releasing" may include a thermoresponsive polymer that thins an encapsulating fibrous layer, thereby substantially outperforming PEG-DA in vivo. Thermoresponsive poly(N-isopropylacrylamide) (PNIPAAm) hydrogels may experience rapid deswelling and reswelling when temperature modulates above and below, respectively, their volume phase transition temperature (VPTT).

The "self-cleaning" thermoresponsive hydrogel membrane may include a double network (DN) design based on PNIPAAm and an electrostatic co-monomer, 2-acrylamido-2-methylpropane sulfonic acid (AMPS). Additionally, the "self-cleaning" thermoresponsive hydrogel membrane may comprise 2-acrylamido-2-methylpropane sulfonic acid and/or an electrostatically charged monomer. DN hydrogels may be comprised of a tightly crosslinked, ionized l"network [P(NIPAAm-co-AMPS)] containing variable levels of AMPS (100:0 to 25:75 wt % ratio of NIPAAm:AMPS) and a loosely crosslinked, interpenetrating 2$^{nd}$ network [PNIPAAm]. AMPS is a strong electrolyte whose sulfonate groups undergo complete dissociation over a wide pH range. Irrespective of AMPS content, the VPTT of the DN hydrogels may be nearly unchanged versus conventional PNIPAAm hydrogels. Thus, while the VPTT of the P(NIPAAm-co-AMPS) 1$^{st}$. network may predictably increase due to the presence of the hydrophilic AMPS comonomer, the "PNIPAAm-only" 2$^{nd}$ network may be able to produce the PNIPAAm hydrogel-like VPTT for the DNs. While conveniently not producing a change to the VPTT, the presence of AMPS in the 1$^{st}$ network may produce improvements in other properties versus conventional SN PNIPAAm hydrogels including extent of swelling, thermosensitivity and compressive strength. These properties may promote glucose diffusion, self-cleaning and the ability to withstand mechanical forces associated with implantation and indwelling. The VPTT of the DN membranes may be raised to above 35° C.

which may be the temperature of a subcutaneous tissue, an expected location of an implanted biosensor. This may render the membrane swollen in the off-state (i.e. no heating), thereby maximizing glucose diffusion. To induce self-cleaning, the membrane may deswell upon transdermal heating above the VPTT (i.e. on-state). The copolymerization of NIPAAm with a hydrophilic comonomer may raise the VPTT of the hydrogel. Small amounts (1-2 wt %) of N-vinylpyrrolidone (NVP) comonomer (based on NIPAAm wt) may elevate the VPTT of the PNIPAAm-based DNNC to ~38° C.-. Thus, NVP may be incorporated into the $2^{nd}$ network of the DN membranes.

To further illustrate various illustrative embodiments of the present disclosure, the following examples are provided.

EXAMPLE 1

Materials and Methods

N-isopropylacrylamide (NIPAAm, 97%), PEG-DA (MW 575 g/mol), and 1-vinyl-2-pyrrolidinone (NVP) were obtained from Aldrich. Acrylamido-2-methylpropane sulfonic acid (AMPS, 97%) and N,N'-methylenebisacrylamide (BIS, 99%) were purchased from ACROS. 2-Hydroxy-2-methyl-1-phenyl-1-propanone (Darocur 1173) was purchased from Ciba Specialty Chemicals (Tarrytown, N.Y.). 1-[4-(2-Hydroxyethoxy)-phenyl]-2-hydroxy-2-methyl-1-propane-1-one (Irgacure 2959) was purchased from BASF. Rat dermal fibroblast cells and growth medium were obtained from Cell Applications (San Diego, Calif.). Lactate dehydrogenase (LDH) cytotoxicity assay kit was obtained from Pierce (Rockford, Ill.). Phosphate-buffered saline (PBS, 1×, pH 7.4) was obtained from Mediatech Inc. (Manassas, Va.).

Preparation of Non-Thermoresponsive PEG-DA Hydrogels

Precursor solutions were formed by vortexing DI-$H_2O$, PEG-DA (100% v/v), and Darocur 1173 (1% v/v) for 1 min Planar hydrogel sheets (~1 mm thick per electronic caliper measurements) were prepared by pipetting the precursor solution between two clamped glass slides (75×50 mm) separated by polycarbonate spacers (1 mm thick) and exposing the mold to longwave ultraviolet (UV) light (UVP UV-Transilluminator, 6 mW cm-2, λ peak=365 nm) for 30 sec at room temperature (RT). Hydrogel sheets were removed from their molds, rinsed with DI $H_2O$, and soaked in a Petri dish containing DI $H_2O$ (60 mL) for 24 hr.

Cylindrical hydrogels (~3 mm×5 mm, diameter x length per electronic caliper) were prepared by pipetting the precursor solution into a hollow cylindrical glass mold (inside diameter=3.0 mm, length=10 mm) with one end sealed by Parafilm. After sealing the other end of the mold, it was likewise exposed to longwave UV light as above at RT for 3 s. The cylindrical hydrogel was removed from the mold, rinsed with DI $H_2O$, and immersed in a Petri dish containing DI $H_2O$ (60 mL) for 24 hr. A clean razor blade was used to equally trim the ends to reduce the length to 5 mm.

Preparation of Thermoresponsive DN Hydrogels

DN hydrogels were prepared by sequential formation of a relatively tightly cross-linked 1st network and a loosely crosslinked 2nd network. The "1st network precursor solution" was formed with NIPAAm monomer, AMPS monomer (the wt % ratio of NIPAAm to AMPS was systematically varied), BIS crosslinker, Irgacure-2959 photo-initiator and DI water. The "2nd network precursor solution" was formed with combining NIPAAm (6.0 g), NVP (0.96 g), BIS (0.012 g), Irgacure 2959 (0.24 g), and DI $H_2O$ (21.0 g).

Planar hydrogel sheets (1 mm thick) were produced by pipetting the first network precursor solution into a mold consisting of two clamped glass slides (75×50 mm) separated by 0.5 or 1 mm thick polycarbonate spacers. The mold was then immersed in an ice water bath (~7° C.) and exposed to longwave UV light for 30 min. The resulting SN P(NIPAAm-co-AMPS) sheet was removed from the mold, rinsed with DI $H_2O$, and then soaked in DI $H_2O$ at RT for 2 days with daily water changes. The SN sheet was then transferred into a covered Petri dish containing the 2nd network precursor solution for 24 hrs at RT. Next, the planar hydrogel was placed into a rectangular mold (1.5 mm thick), photocured for 30 min, and finally soaked in DI $H_2O$ as above.

Cylindrical hydrogels (~3 mm×5 mm, diameter×length) were prepared by pipetting the precursor solution into a cylindrical glass mold (inside diameter=1 or 3 mm, length=10 mm) as above. The mold was immersed in an ice water bath (~7° C.) and exposed for 10 min to longwave UV light. Cylindrical hydrogels were removed from their molds, rinsed with DI $H_2O$, and soaked in a Petri dish containing DI $H_2O$ (60 mL) for 2 days at RT with daily water changes. A SN cylindrical hydrogel was then transferred into a Petri dish containing the second network precursor solution for 24 hrs at RT. The cylindrical hydrogel was then placed into a second cylindrical mold (diameter=~3 mm, length=15 mm), submerged in an ice water bath (~7° C.), exposed for 10 min to longwave UV light, and soaked in DI $H_2O$ as above. A clean razor blade was used to trim ends to reduce the cylindrical length to 5 mm.

Measurement of VPTT

The VPTT of the P(NIPAAm-co-AMPS)/PNIPAAm DN hydrogels were measured with differential scanning calorimetry (DSC; TA Instruments Q100). After soaking in DI-water at RT, the hydrogel specimens were blotted with a Kim Wipe and sealed in a hermetic pan. After cooling to −50° C., the temperature was increased to 50° C. at a rate of 3° C. per min for 2 cycles. The resulting endothermic phase transition peak may be characterized by the initial temperature at which the endotherm starts ($T_o$) and the peak temperature of the endotherm ($T_{max}$). Reported data are from the 2nd cycle.

Glucose Diffusion

Planar hydrogel strips (1 cm×1 cm×1 mm) were placed in a side-by-side diffusion cell (PermeGear, Bethlehem, Pa.) positioned atop a stir plate. The donor chamber contained 3 mL of glucose solution (~1000 mg dL-1), and the receptor chamber contained 3 mL of DI $H_2O$. Chamber solutions were stirred with Teflon-coated stir bars (800 rpm) to maintain constant solution concentrations. A water jacket maintained the designated temperature (35 and 40° C.) throughout the system. Every 10 min (for a total time of 3 h), 50 µL aliquots were removed via pipet from each chamber and glucose concentration was determined with a YSI 2700 Select Biochemistry Analyzer (YSI Incorporated, Yellow Springs, Ohio). The diffusion coefficients were calculated using Fick's second law of diffusion.

Glucose Diffusion Lag Time

A computational model of the DN hydrogels was developed using COMSOL Multiphysics software (COMSOL, Inc., Los Angeles, Calif.). Conducting a time dependent transport of diluted species study, a geometric cylinder (3 mm×5 mm, diameter×length) was constructed with a maximum and minimum free tetrahedral mesh element size of 0.382 and 0.0249 mm, respectively. The simulation began with a DN hydrogel internal glucose quantity of 0 mg dL-1 and external glucose levels of 60, 80, 160, and 300 mg dL-1. The average glucose concentration within the cylindrical hydrogel was assessed every second for 1 hr for each external glucose concentration. The diffusion lag time was defined as the time required for the hydrogel internal glucose concentration to fall within 5% of the external glucose concentration.

Thermosensitivity

Three cylindrical DN hydrogels (~3 mm×5 mm, diameter×length) were vertically attached to a single Petri dish with a small amount of optical adhesive (Norland Optical Adhesive 61) to the base of one end. To hydrate the affixed cylinders, the Petri dish was filled with DI $H_2O$ for at least 12 hrs at RT prior to thermal cycling. The Petri dish was positioned atop a heating plate under a DSLR camera (Canon Rebel T3i) with a 50 mm macro lens. Images were taken every 5 min as the hydrogels were thermally cycled between 25° C. and 40° C. for 5 cycles. The average rate of heating to 40° C. was ~0.7° C./min, and passive cooling to 25° C. was ~0.22° C./min Thus, each cycle consisted of a 1 hr heating period followed by 1 hr of passive cooling. Cylinder diameters were analyzed by ImageJ software.

Cytocompatibility

DN hydrogel cytocompatibility was assessed by measuring LDH concentrations released by rat dermal fibroblast cells 24 hrs after cell seeding versus that of two cytocompatible controls, a PEG-DA hydrogel as well as tissue culture plastic (i.e., polystyrene, PS). Planar DN and PEG-DA hydrogel sheets were prepared as described above. Three 6 mm discs were punched from the sheet and then sterilized by immersion in 80% EtOH for 45 min The hydrogel discs were then washed 3× (30 min each) with sterile PBS, submerged in PBS for 24 hrs, and subsequently transferred to a sterile 24-well plate. Next, rat dermal fibroblast cells suspended in rat fibroblast growth medium, were seeded onto each hydrogel disc and also into the empty tissue culture plastic wells at a concentration of ~6500 cells $cm^{-2}$. Cells were incubated for 24 hrs at ~37° C. with 5% $CO_2$. Finally, the media from each well was extracted and assessed for LDH level per the manufacture's protocol. The relative LDH activity was calculated by normalizing DN sample absorption to that of PS.

Figure 4:
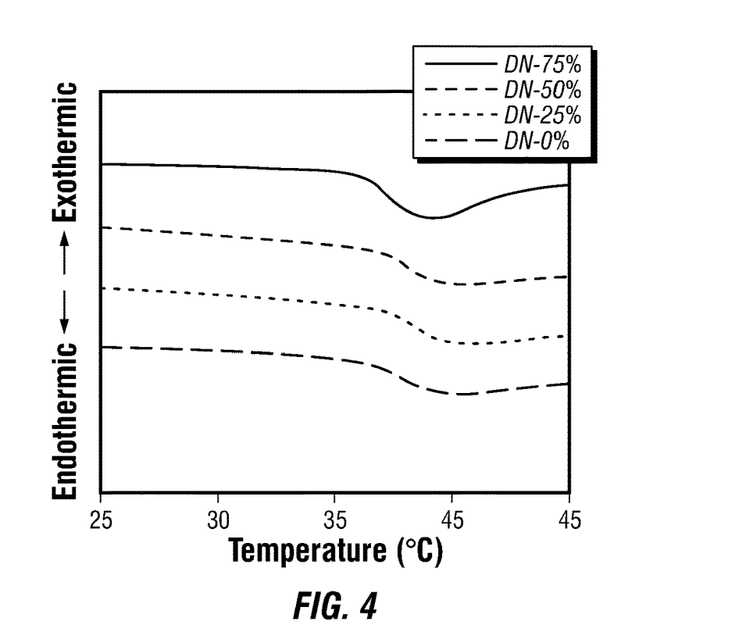
FIG. 4 illustrates differential scanning calorimetry thermograms of thermoresponsive hydrogels in accordance with embodiments.
Figure 5A:
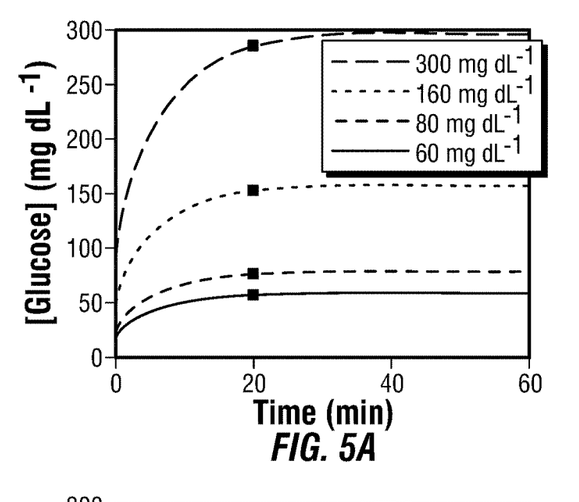
FIG. 5 illustrates average glucose concentration inside cylindrical hydrogels at 35° C. for varying glucose levels.
Figure 5B:
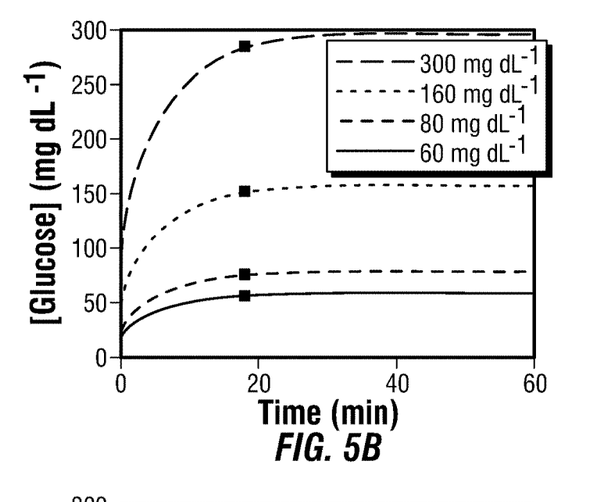
Figure 5C:
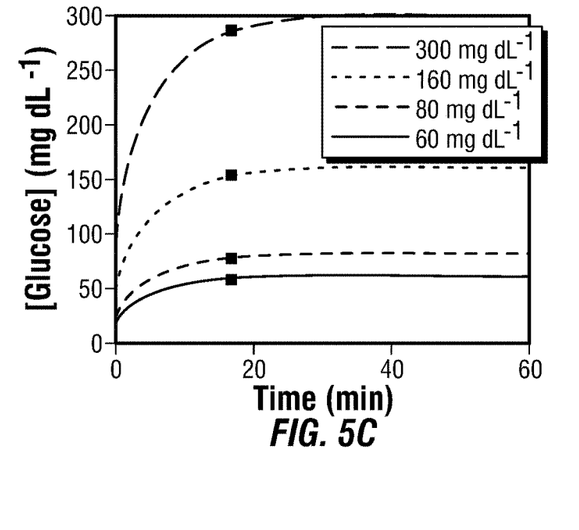
Figure 5D:
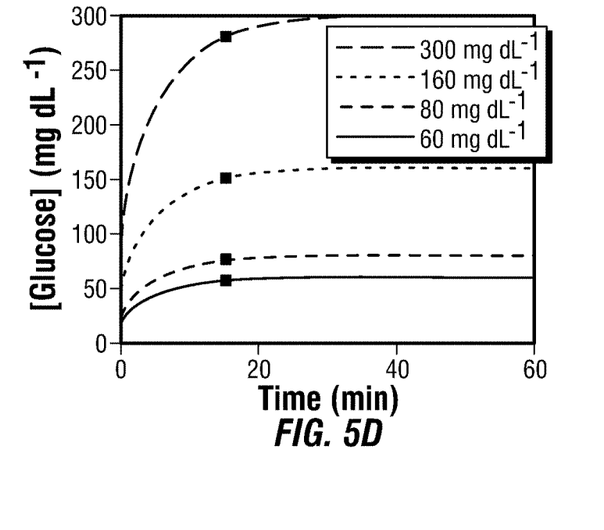

Incorporation of a hydrophilic comonomer is known to increase in the VPTT of thermoresponsive hydrogels. The VPTT of the $1^{st}$ network in the P(NIPAAm-co-AMPS)/PNIPAAm system has been observed to increase with AMPS content. Thus, the NVP comonomer was incorporated into the $2^{nd}$ network precursor solution to adjust the VPTT above the subcutaneous body temperature of the wrist (~35° C.). Herein, in order to achieve a swollen "off-state" (i.e. VPTT>35° C.), 2% NVP (based on NIPAAm weight) was incorporated into the $2^{nd}$ network. Per the DSC thermograms, illustrated by FIG. 4, $T_o$ and $T_{max}$ of all compositions were all close in value and greater than 35° C. with $T_{max}$ approximately equal to ~39.6° C. as shown in Table 1.

The diffusion coefficient at 35° C. and 40° C. was assessed by examining glucose diffusion through the membrane sandwiched between side-by-side diffusion cell systems. Fick's $2^{nd}$ law of diffusion was used to calculate the diffusion coefficients at each temperature:

$$\frac{\partial c}{\partial t} = D \frac{\partial^2 c}{\partial z^2}$$

Where c is the concentration within the hydrogel, t is the time, D is the diffusion coefficient, and x is the diffusion distance. The above equation may be modified based on the assumption that each solution preserved a uniform concentration and that each element concentration was equal at the hydrogel membrane surface as in the bulk volume of each chamber. The simplified equation is:

$$Q_t = \frac{ADC_1}{L}\left(t - \frac{L^2}{6D}\right)$$

Where $Q_t$ is the overall quantity of glucose transferred through the hydrogel until the specific time, t, A refers to the hydrogel area exposed to the donor or receiving chambers, $C_1$ is the initial solute concentration of the donor chamber, and L is the measured hydrogel membrane thickness. The results of the study are shown in Table 2. At 35° C. (T<VPTT), the DN hydrogel membranes were at the swollen state. D of glucose through the dermis and epidermis have been reported as $2.64\pm0.42\times10^{-6}$ and $0.075\pm0.05\times10^{-6}$ $cm^2/s$, respectively. Thus, the determined value of D ($1.82\pm0.02\times10^{-6}$ $cm^2/s$) for DN-0% (i.e. AMPS:NIPAAm=0:100 wt %) is within the functional range. Moreover, glucose diffusion was similar versus a PEG-DA membrane and DN which were previously determined to be $1.59\pm0.42\times10^{-6}$ $cm^2/s$ and $1.88\pm0.01\times10^{-6}$ $cm^2/s$ respectively. As AMPS content increased, the value of D also increased which can be attributed to a more swollen membrane caused by increased electrostatic repulsion. When temperature was heated to 40° C. (T>VPTT), the membranes became deswollen. As expected, this reduced glucose diffusion as indicated by the decreased values of D. Overall, these results verify satisfactory glucose diffusion through the DN hydrogels in the "off-state". During deswelling (i.e. self-cleaning), glucose measurements may be likely prohibited.

A COMSOL Multiphysics computational model was utilized to determine the glucose diffusion lag time for the DN cylindrical hydrogels (diameter 1.5 mm, length 5 mm). The simulation utilized an initial glucose quantity within the

TABLE 1

Glucose diffusion coefficient (D) of hydrogels below and above the VPTT.

| AMPS:NIPAAm | Notation | VPTT $T_o$(° C.) | $T_{max}$(° C.) | 35° C. Average D ($cm^2/s$) | 40° C. Average D ($cm^2/s$) |
|---|---|---|---|---|---|
| 0:100 | DN-0% | 36.8 | 39.7 | $1.82 \pm 0.02 \times 10^{-6}$ | $1.16 \pm 0.02 \times 10^{-6}$ |
| 25:75 | DN-25% | 37.3 | 39.9 | $1.99 \pm 0.01 \times 10^{-6}$ | $0.66 \pm 0.02 \times 10^{-6}$ |
| 50:50 | DN-50% | 37.1 | 39.8 | $2.06 \pm 0.03 \times 10^{-6}$ | $0.75 \pm 0.01 \times 10^{-6}$ |
| 75:25 | DN-75% | 36.2 | 39.1 | $2.21 \pm 0.02 \times 10^{-6}$ | $1.04 \pm 0.03 \times 10^{-6}$ | hydrogel was set to 0 mg dL$^{-1}$. Subsequently, four different glucose concentrations (60, 80, 160, and 300 mg dL$^{-1}$) that represent low, normal, high and very high physiologically glucose levels were applied to the cylinders. With these conditions, the average glucose concentration within the hydrogel cavity every second up to 1 hr was calculated as shown in FIG. 5. For DN-0% hydrogel, an average lag time of 19.01±0.22 min was observed, which is similar to the DN. However, as AMPS levels were increased, lag time systematically decreased and the lag time of DN-75% was reduced to 15.48±0.15 min as shown in Table 2.

TABLE 2

Diffusion lag times of hydrogel computational models.

| Notation | Diffusion Lag Time (min) |
|---|---|
| DN-0% | 19.01 ± 0.22 |
| DN-25% | 17.29 ± 0.09 |
| DN-50% | 16.67 ± 0.26 |
| DN-75% | 15.48 ± 0.15 |

The increase in pore size and hydration may be responsible for the reduction in lag time. Physiological lag times upward of 15 min have been reported between glucose changes in the interstitial fluid (ISF) and in the blood. To further reduce the lag time, the cylinder diameter may be reduced. If a lag time of less than 5 min is targeted, the maximum diameters for DN hydrogels are shown in Table 3.

TABLE 3

Max diameter for a lag time less than 5 min.

| Notation | Max Diameter (μm) |
|---|---|
| DN-0% | 346 |
| DN-25% | 394 |
| DN-50% | 403 |
| DN-75% | 417 |

The extent and rate at which the cylindrical hydrogel deswells and reswells upon cyclically heating (T>VPTT) and cooling (T<VPTT) is critical for its ability to function as a self-cleaning membrane. The thermosensitivity of hydrogels were determined by measuring the diameter change during thermal cycling. The diameter of a vertically affixed charged DN

TABLE 4

Diameter decrease from swollen to deswollen state.

| Notation | Max Diameter Change (%) |
|---|---|
| PEG | N/A |
| DN | 24.8 ± 0.7 |
| DN-0% | 22.7 ± 2.1 |
| DN-25% | 24.7 ± 1.7 |
| DN-50% | 25.2 ± 1.7 |
| DN-75% | 33.2 ± 1.0 | hydrogel (DN-25%, 50%, and 75%) cylinders showed more dramatic diameter change at 40° C. compared to pure DN-0%. DN-75% exhibited a greater extent of diameter change versus DN as shown in Table 4.

Figure 6:
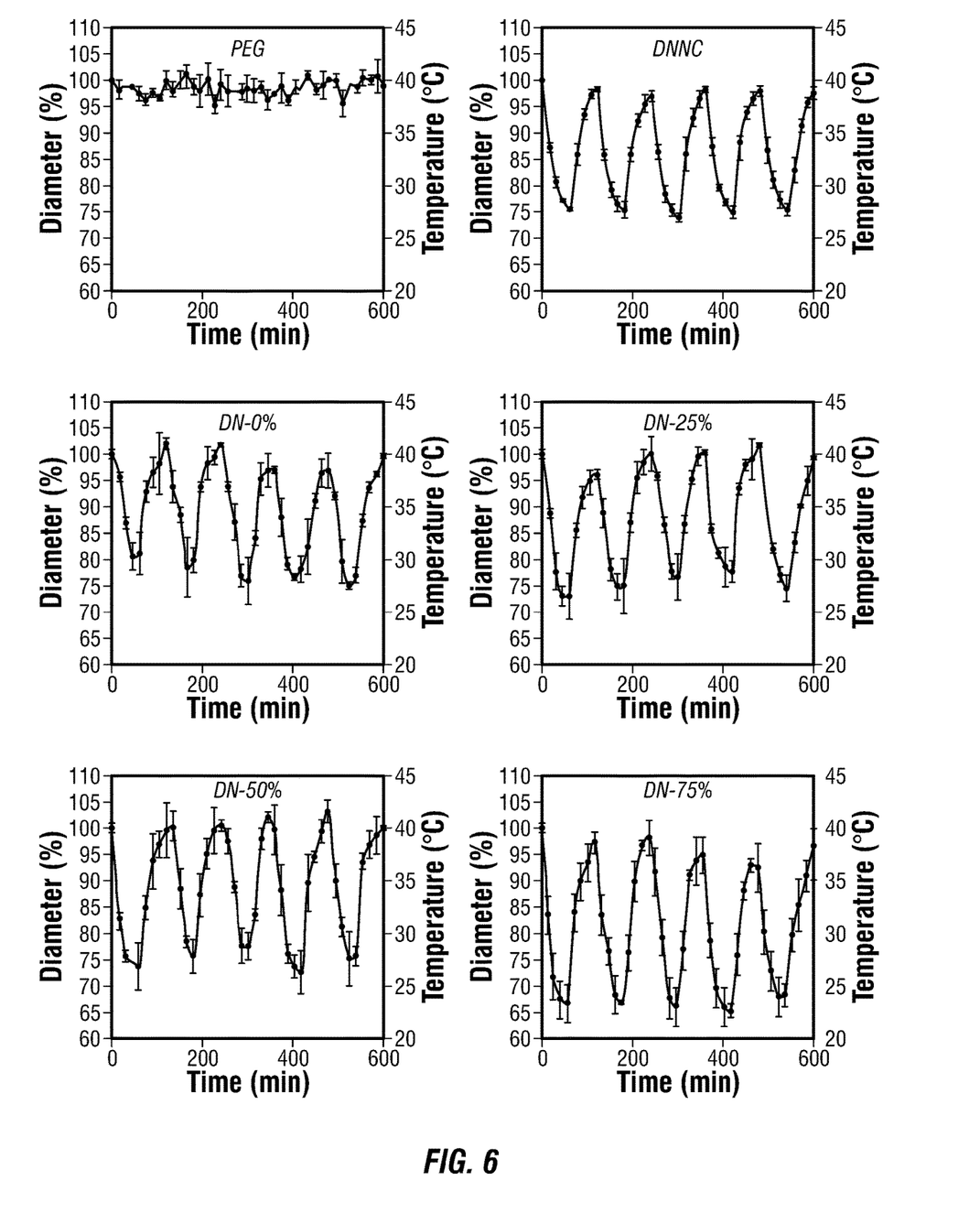
FIG. 6 illustrates the diameter change during thermal cycling of a vertically affixed hydrogel cylinder over a 10 hr time period.

After cooling to 25° C. for a period of 1 hr, the diameters of specimens all returned to within 95% of its initial measured swollen state. The reversible thermo-transition was confirmed by cyclical heating (~0.70° C./min) and cooling (~0.22° C./min) over a 10 hr period as illustrated by FIG. 6. A consistent change in diameter during each cycle was observed.

Figure 7:
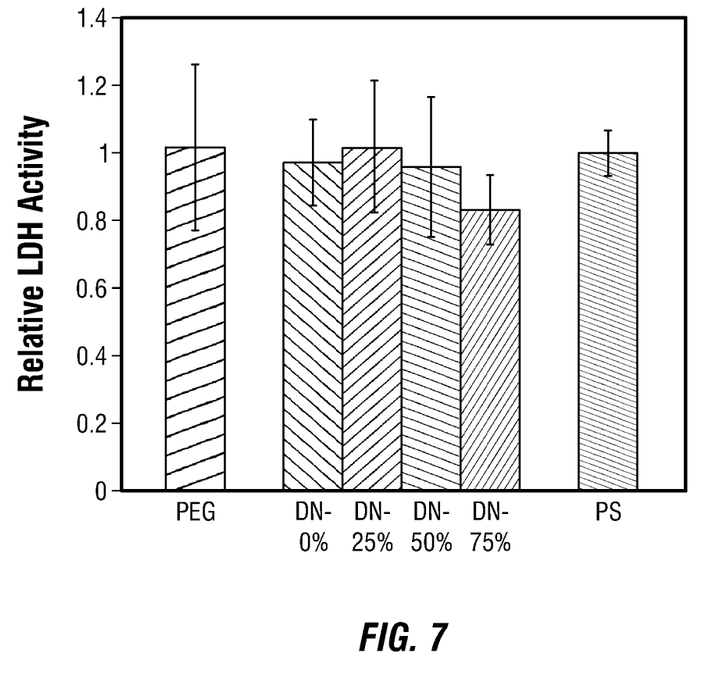
FIG. 7 illustrates the relative lactate dehydrogenase activity amongst different of thermoresponsive hydrogels after 24 hrs.

A high degree of cytocompatibility may be a desired prerequisite for a subcutaneously implanted self-cleaning membrane to be applied in clinic. The cytocompatibility of the hydrogels was assessed via lactate dehydrogenase (LDH) activity assays. LDH is a biomarker released during tissue damage, thus can be measured to determine cellular toxicity. LDH levels of different specimens released by rat dermal fibroblast cells 24 hr postseeding were analyzed. Compared to the LDH levels of non-cytotoxic PEG-DA hydrogel and tissue culture plastic (i.e. PS), All of the P(NIPAAm-co-AMPS)/PNIPAAm membranes exhibited similar values, which indicate low cytotoxicity toward fibroblast cells as illustrated by FIG. 7.

"Self-Cleaning" In Vivo.

Cylindrical PEG-DA (control) and DNNC (diameter~1.5 mm, length~5 mm) membranes were sterilized by exposure to 80% ethanol for 45 minutes. All hydrogel rods were then washed three separate times for 30 minutes with sterile Dulbecco's phosphate buffer solution. Disposable, sterile trocar needles (13 G; inner diameter=1.804 mm, Avid Identification Systems, Inc.) were utilized to inject one of each cylindrical polymer into the subcutaneous tissue (2-3 mm in depth) on the dorsal of CD® Hairless rats (N=20, male, 8 weeks old, Charles River Laboratories). The CD Hairless rat specie encompasses a normal immune response despite its abnormal, reduced hair growth. The rat's hairless characteristic is ideal to facilitate the membrane implantation without unwarranted skin irritation commonly associated with shaving and nairing. Using isoflurane by inhalation, animals were anesthetized and anesthesia depth was tested by foot pinch reaction. Following implantation, the injection site was closed with surgical adhesive (3M VETBOND™ Tissue Adhesive, No. 1469SB). Material composition and dorsal placement were recorded for each rat/implant. All animals were immediately returned to individual cages and monitored every 12 hours. A custom designed LabView program (National Instruments) recorded cage temperatures every 5 mins. After either 7 or 30 days post implantation, 10 animals were euthanized by $CO_2$ asphyxiation, photographed, and evaluated for gross changes and immediately fixed in 10% neutral buffered formalin for one week. Finally, implants and their surrounding tissue were removed and processed for histology by serial dehydration, paraffin embedding, sectioning, and staining (hematoxylin and eosin (H&E)).

EXAMPLE 2

Materials

Poly (diallyldimethylammonium chloride) (PDAD-MAC$^+$) solution, poly (sodium 4-styrenesulfonate) powder (PSS$^-$), and poly (4-styrenesulfonic acid-co-maleic acid) powder (PSS/co-polymer$^-$) were purchased from Sigma (St. Louis, Mo.). Sodium bicarbonate was purchased from AVANTOR™ Performance Materials (Center Valley, Pa.). Rhodamine isocyanate poly (allylamine) (RITC-PAH$^+$) was synthesized by Ashvin Nagaraja at Texas A&M University. The AMPS PNIPAAm hollow rod gel was synthesized as previously described. All buffers were made using deionized water (DI $H_2O$) with a resistance of ~18.2 MΩ·cm.

Modification of AMPS PNIPAAm Gel for the Encapsulation of Glucose Sensing Assay.

A. Layer by Layer Hydrogels for Direct Embedding of Assay.

The following poly electrolyte solutions were prepared at pH 8 in 5 mM sodium bicarbonate buffer: PDADMAC+ (2 mg/mL), PSS− (2 mg/mL), and RITC-PAH+ (2 mg/mL). The hydrogel was then connected to inlet and outlet needles. Next, the inner surface of the hydrogel was washed by flowing 5 mL of DI $H_2O$ through the gels three times, via a 5 mL syringe. The layers were then deposited starting with the positively charged polyelectrolyte due to the negative nature of the gel. Briefly, 1 mL of PDADMAC+ was deposited first on the inner walls of the hollow rod hydrogel via a syringe needle. After 1 minute, 5 mL of DI $H_2O$ was injected into the gel to wash away any residue that did not attach electrostatically to the wall. Following this wash, 1 mL of PSS− was injected in a similar manner into the gel and after allowing it to interact with the previous layer for 1 minute the inner walls were again washed with 5 mL of DI $H_2O$. This was repeated until a total of 5 bilayers were deposited. For imaging purposes, an additional 5 Bilayers of RITC-PAH+/PSS− was deposited on the inner wall of the hydrogel rod in a similar manner RITC-PAH+ allow for the imaging of the layers via fluorescence microscope. The gel was then flushed 3 times with DI $H_2O$ to remove any unconjugated poly-electrolyte. Bright-field and fluorescence images were then taken via a Nikon Eclipse TE2000-U Inverted Microscope (Nikon Instruments Inc., Melville, N.Y.).

B. Layer by Layer Hydrogels for Immobilization of Competing Ligand.

The following poly electrolyte solutions were prepared at pH 8 in 5 mM sodium bicarbonate buffer: PDADMAC+ (2 mg/mL), PSS− (2 mg/mL), PSS/co-polymer− (2 mg/mL) and RITC-PAH+ (2 mg/mL). Similar to the method above, 5 bilayers of PDADMAC+/PSS− were deposited first, followed by 5 bilayers of PDADMAC+/PSS co-polymer−. The PSS co-polymer− provided free carboxylic acid groups which allowed for the conjugation of amine reactive groups. For this work, bi-functional poly ethylene glycol amine (NH2-PEG-NH2) purchased from Nanocs Inc. was then conjugated to these free carboxylic acid using the traditional 1-ethyl-3-[3-dimethylaminopropyl] carbodiimide EDC (1-ethyl-3-[3-dimethylaminopropyl] carbodiimide)/NHS (sulfo-NHS) reaction. Briefly, 1 mL of EDC/NHS in 0.1M (2-[morpholino]ehtanesulfonic acid) buffer (pH 6) was injected into the hollow cavity and allowed to react for 15 minutes followed by 1 mL of $NH_2$-PEG-$NH_2$ dissolved in 0.1 M phosphate-buffered saline. This solution was allowed to react for 2 hours before flushing the cavity with DI $H_2O$ to remove any unconjugated PEG. Next, the competing ligand, which is fluorescently labeled with amino-pyrene trisulfonyl chloride, was dissolved in 1 mL of triethylamine and acetonitrile and injected into the cavity. After an incubation time of 15 minutes, which allowed for the functionalization of the competing ligand to the PEG linker, the cavity was washed three times with DI $H_2O$ to remove all unconjugated fluorescently labeled competing ligand. Fluorescence images were then taken via a Nikon Eclipse TE2000-U Inverted Microscope.

C. Glucose Diffusion Study through Layer by Layer Hydrogel.

The purpose of these layer-by-layer (LbL) hollow rod hydrogels is to act as a biocompatible housing mechanism for a glucose sensing assay. Therefore, glucose diffusion studies were conducted at room temperatures on 3 different hydrogels to determine whether the presence of the layer hindered the diffusion rate of glucose through the gel.

For this study, approximately 1 mm thick 25% AMPS PNIPAAm hydrogel slabs was synthesized. Using an open-face filter holder (Pall Co., Port Wash., N.Y.), the hydrogel slab was securely clamped between the ring which allowed for only one side of the hydrogel to be exposed for LbL modification. The exposed side was washed 3 times with 10 mL DI $H_2O$ and then 10 bilayers of PDADMAC+/PSS− were deposited on the exposed surface, using similar method described in 1.2. The hydrogel was then removed from the filter holder and the side with the layers was marked as a means of identification in the future. The gels were then allowed to soak in DI $H_2O$ for 48 hours with new water exchange approximately every 12 hours.

The LbL hydrogel was then cut into smaller strips (1 cm×1 cm) and placed in side-by-side diffusion chambers (PermeGear, Bethlehem, Pa.) with the LbL side facing the receiver chamber containing 3 mL DI $H_2O$. The donor chamber contained 3 mL glucose solution (~1000 mg/dL). The chambers were mounted on a stir plate set to 1000 rpm to ensure that the concentration in both chambers remained constant. In 20 minute intervals, 50 µL of solution was extracted from each chamber via a pipette for a period of 3 hours. A YSI 2700 Select Biochemistry Analyzer (YSI Incorparated, Yellow Springs, Ohio) was then used to determine the concentration of glucose present in the extracted samples. Then the diffusion coefficient was calculated using a derivative form of Fick's second law of diffusion. This study was conducted on three LbL hydrogels and three non-layered hydrogels were used as controls at room temperature.

Bulking Up of Competing Ligand for Encapsulation.

A. PEGylation of Fluorescent Dye Conjugated to Competing Ligand.

The size of the competing ligand can also be increased in order to ensure encapsulation of the glucose sensing assay within the hydrogel with no leaching. PEGylation can be utilized for this purpose. The schematic below illustrates the process by which poly ethylene glycol chains can be conjugated to the fluorescently labeled competing ligand via its fluorophore. The fluorophore, amino-pyrene trisulfonyl chloride (compound 1) dissolved in $CH_2CN$ is allowed to react at room temperature with monofunctional PEG-amine dissolved in DIEA for at least an hour. The solvent is then removed under pressure and re-dissolved in $DIH_2O$. The solution was purified via dialysis using a 1 k Da molecular weight cut off membrane from Spectrum® Labs and absorbance scan was taken to verify conjugation of the PEG chains. Following PEGylation, the competing ligand can then be conjugated to the modified fluorophore via reductive amination reaction.

Fluorescence Image of L-b-L on Inner Hydrogel Wall.

The poly-electrolyte layers adhered to inner wall of the hydrogel. Furthermore, based on the absence of fluorescence within the walls of the hydrogels, the poly-electrolytes did not diffuse into the walls of the hydrogel.

Fluorescence Image of L-b-L Hydrogel with Immobilized Fluorescently Labeled Competing Ligand.

Based on the fluorescence image, the competing ligand was successfully immobilized on the inner wall of the AMPS PNIPAAM hydrogel.

Glucose Diffusion Study.

The average glucose diffusion coefficient of the LbL hydrogels was $2.68 \times 10^{-6} \pm 0.35$ $cm^2/s$. When compared to the gels without the layers whose average diffusion coefficient was $2.61 \times 10^{-6} + 0.62$ cm$^2$/s. Therefore, the presence of the layers did not appear to hinder the ability for glucose to diffuse through the gels.

PEGylation of Fluorescent Dye Conjugated to Competing Ligand.

The absorbance scan indicates 20 nm wavelength shifts for the PEGylated fluorophore. This may confirm that the PEG chains are attached to the fluorophore.

Although the present disclosure and its advantages have been described in detail, it should be understood that various changes, substitutions and alterations may be made herein without departing from the spirit and scope of the disclosure as defined by the appended claims.

What is claimed is:

1. A method for cleaning an implanted glucose biosensor comprising:
    providing a glucose biosensor comprising a double network thermoresponsive hydrogel membrane comprising:
        a first network and a second network;
        N-isopropylacrylamide (NIPAAm) present in the first network and the second network;
        an electrostatic monomer of 2-acrylamido-2-methylpropane sulfonic acid (AMPS) present in the first network such that the ratio of AMPS:NIPAAm is about 25:75 to about 75:25 wt. % in the first network; and
        a comonomer of N-vinylpyrrolidone (NVP) present in the second network in an amount between about 1 to about 2 wt. % based on weight of the NIPAAm, wherein the presence of NVP in the second network increases a volume phase transition temperature (VPTT) of the overall membrane to about 38° C.;
    wherein the membrane is self-cleaning,
    wherein the membrane is a cylinder comprising a diameter measuring about 1.5 mm and a length measuring about 5 mm, and
    wherein the glucose biosensor measures a concentration of glucose; and
    implanting the glucose biosensor into a target area;
        wherein temperature fluctuations within the target area that exceed the VPTT induce deswelling in the membrane and temperature fluctuations within the target area that fall below the VPTT induce swelling in the membrane, wherein the temperature fluctuations are induced physiologically within a body, and wherein the deswelling or swelling cleans the glucose biosensor.

2. The method of claim 1, wherein the membrane comprises poly(N-isopropylacrylamide).

3. The method of claim 1, wherein the membrane is cross linked.

4. The method of claim 1, wherein the membrane further comprises poly-electrolyte layers.

5. The method of claim 1, wherein the deswelling of the membrane induces the removal of at least a portion of any attached cells from the membrane.

6. An implantable medical device comprising a double network thermoresponsive hydrogel membrane comprising a first network and a second network, wherein the membrane is self-cleaning, wherein the membrane is a cylinder comprising a diameter measuring about 1.5 mm and length measuring about 5 mm, and wherein the membrane comprises:
    N-isopropylacrylamide (NIPAAm) present in the first network and the second network,
    an electrostatic monomer of 2-acrylamido-2-methylpropane sulfonic acid (AMPS) present in the first network such that the ratio of AMPS:NIPAAm is about 25:75 to about 75:25 wt. %, and
    N-vinylpyrrolidone (NVP) present in the second network in an amount between about 1 to about 2 wt. % based on weight of the NIPAAm, wherein the presence of NVP in the second network increases a volume phase transition temperature (VPTT) of the overall membrane to about 38° C.,
    wherein cyclic temperature fluctuations of the membrane around the VPTT cause cyclic deswelling and swelling of the membrane, wherein the cyclic temperature fluctuations are induced physiologically within a body.

7. The device of claim 6, wherein the deswelling of the membrane induces the removal of at least a portion of any attached cells from the membrane.

* * * * *